United States Patent
Plank et al.

(10) Patent No.: US 7,621,145 B2
(45) Date of Patent: Nov. 24, 2009

(54) HIGH-PRESSURE FREEZING DEVICE, AUTOMATIC APPARATUS FOR LOADING SPECIMENS INTO A HIGH-PRESSURE FREEZING DEVICE, AND METHOD FOR LOADING A HIGH-PRESSURE FREEZING DEVICE

(75) Inventors: Heinz Plank, Wr. Neudorf (AT); Andreas Hallady, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 261 days.

(21) Appl. No.: 11/268,600

(22) Filed: Nov. 2, 2005

(65) Prior Publication Data

US 2006/0090481 A1  May 4, 2006

(30) Foreign Application Priority Data

Nov. 3, 2004  (DE) ........................ 10 2004 053 073

(51) Int. Cl.
*F25D 3/00* (2006.01)
(52) U.S. Cl. ........................... 62/293; 62/378; 83/915.5
(58) Field of Classification Search .................. 62/374, 62/378, 293, 51.1; 83/915.5
See application file for complete search history.

(56) References Cited

U.S. PATENT DOCUMENTS

| | | | | |
|---|---|---|---|---|
| 4,388,814 A | * | 6/1983 | Schilling | 62/62 |
| 4,551,992 A | * | 11/1985 | Sitte et al. | 62/51.1 |
| 5,299,481 A | * | 4/1994 | Lihl et al. | 83/170 |
| 5,493,865 A | | 2/1996 | Wohlwend | 62/51.1 |
| 5,761,977 A | * | 6/1998 | Jakobi et al. | 83/13 |
| 6,178,757 B1 | * | 1/2001 | Sitte et al. | 62/126 |
| 6,269,649 B1 | | 8/2001 | Studer | 62/51.1 |
| 6,860,113 B2 | * | 3/2005 | Goll | 62/126 |
| 7,293,426 B2 | * | 11/2007 | Heuser | 62/373 |

OTHER PUBLICATIONS

Leica Mikrosysteme GmbH, Leica Microsystems, Leica EM PACT, High Pressure Freezer, Dec. 2000, Vienna, Austria.
Leica Mikrosysteme GmbH, Leica Microsystems, Leica EM PACT, Microbiopsy Transfer System, Dec. 2003, Vienna, Austria, available at http://www.em-preparation.com.
Leica Mikrosysteme GmbH, Leica Microsystems, Leica EM PACT, Flat Specimen System, Dec. 2003, Vienna, Austria, available at http://www.em-preparation.com.
BAL-TEC AG, EM Technology And Application, HPM 010 High Pressure Freezing Machine, pp. 1-7, Feb. 10, 2000, available at http://www.bal-tec.com.

* cited by examiner

*Primary Examiner*—William E Tapolcai
(74) *Attorney, Agent, or Firm*—Simpson & Simpson, PLLC

(57) ABSTRACT

An automatic loading apparatus (12) for specimens (1) for high-pressure cryosubstitution is disclosed. The automatic loading apparatus (12) is connected to a high-pressure freezing device (40). Specimens (1) are inserted in a holder (2). By means of a slider (4), the specimens (1) and holders (2) are conveyed to the automatic loading apparatus (12). The guidance element (26) allows exact positioning of the holder (2) in the clamping element (14). The automatic loading apparatus makes possible rapid transfer of the holder (2) having the specimen (1) from, for example, an optical microscope to the high-pressure freezing device (40).

11 Claims, 7 Drawing Sheets

HIGH-PRESSURE FREEZING DEVICE, AUTOMATIC APPARATUS FOR LOADING SPECIMENS INTO A HIGH-PRESSURE FREEZING DEVICE, AND METHOD FOR LOADING A HIGH-PRESSURE FREEZING DEVICE

CROSS REFERENCE TO RELATED APPLICATIONS

This application claims priority of the German patent application 10 2004 053 073.4, filed Nov. 3, 2004, which is incorporated by reference herein.

FIELD OF THE INVENTION

The invention concerns a high-pressure freezing device. The invention concerns in particular a high-pressure freezing device having a chamber in which the high-pressure freezing takes place, the sample with holder being retained in a clamping element, and having a reservoir of liquid nitrogen.

The invention further concerns an automatic apparatus for loading specimens into a high-pressure freezing device.

The invention additionally concerns a method for loading a high-pressure freezing device.

BACKGROUND OF THE INVENTION

U.S. Pat. No. 6,269,649 B1 discloses a system for freezing samples under high pressure. The high pressure is necessary in order to prevent the formation of ice crystals in the sample. The sample is located in a sample holder and is clamped into a corresponding sample carrier. The sample carrier is manually transferred into the high-pressure freezing system by the user thereof.

U.S. Pat. No. 5,493,865 discloses a method and an apparatus for high-pressure freezing of biological samples. Before high-pressure freezing, the sample is introduced manually into the sample holder.

At present it is necessary, usually using a stereomicroscope, to fill the small specimen holders that are used in a high-pressure freezing device with a sample. That specimen holder is then installed into a holder for the high-pressure freezing device, and that holder is then inserted into the high-pressure freezing device. Insertion of the holder into the high-pressure freezing device is accomplished manually. The Leica EM PACT brochure discloses a high-pressure freezing device. This system operates with separate pressure and cooling systems. The consequence of this is that the specimen must be threaded in pressure-tight fashion into the sample holder. The Leica EM PACT brochure entitled "Microbiopsy Transfer System" and the Leica EM PACT brochure entitled "Flat Specimen System" disclose several installation aids for specimen holders and tools for manual transfer of the samples, secured in the sample holder, to the high-pressure freezing device.

The brochure of the company styled BAL-TEC AG likewise discloses an apparatus for high-pressure freezing. In this unit, pressure buildup is ensured by way of the cooling medium. Although pressure-tight threading of the specimen holder is not necessary, a loading apparatus and a holder for the specimen carrier are necessary. The time for installation of the specimen carrier and introduction of the specimen carrier into the loading apparatus is also approximately one minute. In addition, the specimen carrier must once again be introduced manually into the high-pressure freezing device.

The disadvantage of the existing art is that more than a minute is required for installation of the samples being examined into a holder provided for them, and for positioning of the holder in a clamping element. In addition, during the threading motion of the clamping element a specific torque must be observed so that the sample to be examined is not mechanically crushed and/or destroyed, which can result in a change in the morphology of the sample to be examined. The sample changes during the aforementioned loading time of approximately one minute, so that the states observed with the optical microscope are no longer present upon examination with an electron microscope. The state of the cells observed with the light microscope differs from the frozen cells. A comparison of the two cells is therefore possible only to a limited extent.

SUMMARY OF THE INVENTION

It is the object of the invention to create a high-pressure freezing device which is configured so that it makes possible a rapid transfer of the samples into the high-pressure freezing device, and so that no morphological changes occur in the unfrozen state and in the frozen state in the sample to be examined.

The aforesaid object is achieved by a high-pressure freezing device that encompasses a chamber in which high-pressure freezing takes place; a specimen with a holder being retained in a clamping element; a reservoir of liquid nitrogen; an automatic loading apparatus connected to the high-pressure freezing device, wherein the automatic loading apparatus is designed to transfer the clamping element into the chamber of the high-pressure freezing device.

A further object of the present invention is to create an automatic loading apparatus for specimens for high-pressure cryosubstitution which makes possible a rapid transfer of the sample into the high-pressure freezing device and likewise rules out mechanical changes in the morphology of the sample.

The aforesaid object is achieved by an automatic loading apparatus for specimens for high-pressure cryosubstitution that encompasses a slider on which is retained a specimen located in a holder; and the loading apparatus comprises at least one guidance element with which the holder is positionable in a clamping element.

A further object of the invention is to describe a method for loading a high-pressure freezing device that makes possible a rapid and reliable transfer of samples into the high-pressure freezing device, so that no morphological differences occur between an unfrozen sample and a frozen sample.

The aforesaid object is achieved by a method that encompasses the steps of:
 positioning a slider, having a holder for a specimen, in a guidance element of a loading apparatus for the high-pressure freezing device;
 clamping the holder in a clamping element; and
 displacing the clamping element, with the clamped holder, into the high-pressure freezing station by means of a pneumatic cylinder.

The automatic loading apparatus according to the present invention for specimens for high-pressure freezing has the advantage that a sample that is first examined with an optical microscope, and is then introduced into an electron microscope for the observation of details that require a higher resolution, experiences little or no change in morphology. A confocal microscope is used, inter alia, to study proteins to which fluorescent markers are attached, in motion in the living cells. The insufficient resolution of the light microscope emerges as a disadvantage in this context. The proteins themselves cannot be identified with the light microscope. The electron microscope has the high resolution required for this, and the automatic loading apparatus according to the present invention thus makes it possible to freeze in place the dynamic state of the cells to be examined in a sample, and also to ensure that no morphological changes occur as a result of installation of the sample in the high-pressure freezing device. The automatic loading apparatus for specimens for high-pressure freezing furthermore has the advantage that, for example, transfer of a specimen from the confocal microscope to the high-pressure freezing device can be accomplished within five seconds. With this short time, it is possible to ensure that, for example, a protein observed with the light microscope is still in the same location when observed with an electron microscope. This time-optimized automatic loading system is implemented by the automatic loading apparatus for specimens for high-pressure freezing.

The automatic loading apparatus for specimens for the high-pressure freezing device is advantageous because it encompasses a slider on which a fork is embodied. The fork comprises two oppositely located limbs, on each of which is embodied a recess in which a specimen, located in a holder, is retained. The loading apparatus possesses at least one guidance element with which the holder is positionable in the clamping element.

The clamping element encompasses a pusher part and a counterelement. A shell that is embodied with two oppositely located openings partially encloses the pusher part and the counterelement.

Also provided is a sensor that records the presence of the slider in the automatic loading station. Additionally provided is a motor that is connected via a shaft to the pusher part of the clamping element.

A control system is provided which establishes, from the power consumption of the motor, a torque-limited threading motion between the counterelement, the holder, and the pusher part.

The loading apparatus further possesses a pneumatic cylinder that introduces the clamping element, with the holder, into a high-pressure freezing station and uncouples the shaft of the motor from the clamping element.

The clamping element possesses a connector tube for the high pressure. The pneumatic cylinder creates, in the high-pressure freezing station, the connection for high pressure to the connector tube of the clamping element.

For examination of the sample or specimen with an optical microscope, a cutout is furthermore shaped into a stage support provided for the microscope. The slider is configured in such a way that the holder having the sample, inserted into the fork, comes to rest on a coverslip located on the stage support.

A further advantage of the present invention is a high-pressure freezing device having a chamber in which high-pressure freezing takes place, the sample with holder being retained in a clamping element. The high-pressure freezing device furthermore possesses a reservoir of liquid nitrogen. The high-pressure freezing device is connected to an automatic loading apparatus, the automatic loading apparatus transferring the clamping element into the chamber of the high-pressure freezing device.

A further advantage of the invention is a method for loading a high-pressure freezing device, in which a specimen located in a holder is placed into a slider. The slider is positioned in a guidance element of a loading apparatus for the high-pressure freezing device. The holder is then inserted, by way of the slider, into the clamping element. The clamping element is closed by way of a torque-limited motor, so that clamping of the holder in the clamping element occurs. The clamping element having the clamped-in holder is slid into the high-pressure freezing station with a pneumatic cylinder, the shaft of the motor being uncoupled from the clamping element. Lastly, a connection for high pressure is created, by the pneumatic cylinder, between the high-pressure freezing station and a connector tube of the clamping element.

Further advantages and advantageous embodiments of the invention may be inferred from the dependent claims and are the subject of the Figures below and their descriptions.

DETAILED DESCRIPTION OF THE INVENTION

Figure 1:
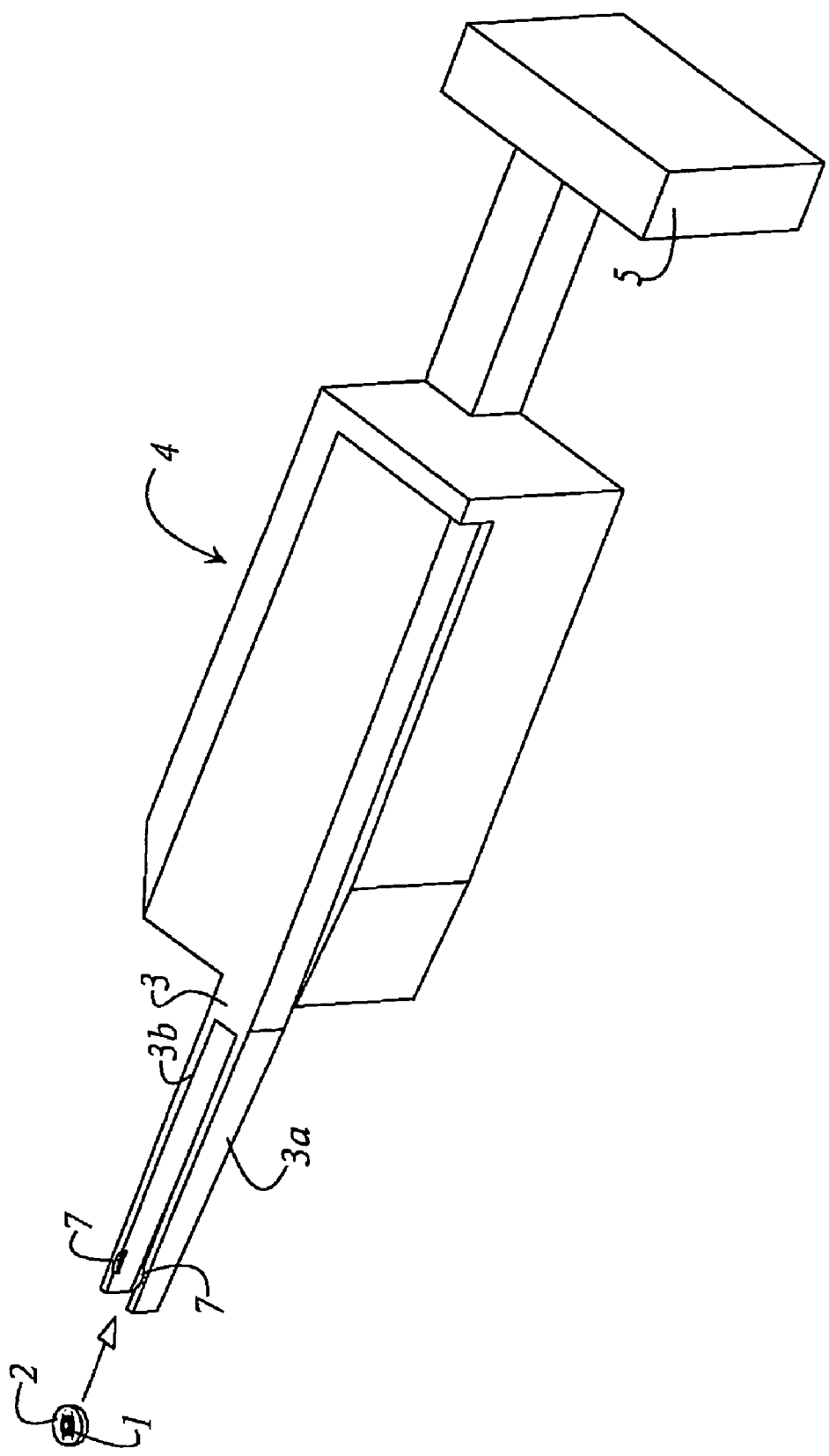
FIG. 1 is a perspective view of a slider for introducing a specimen, located in a holder, into a high-pressure freezing device, or for positioning the holder having the specimen on a microscope stage for optical examinations.
Figure 5:
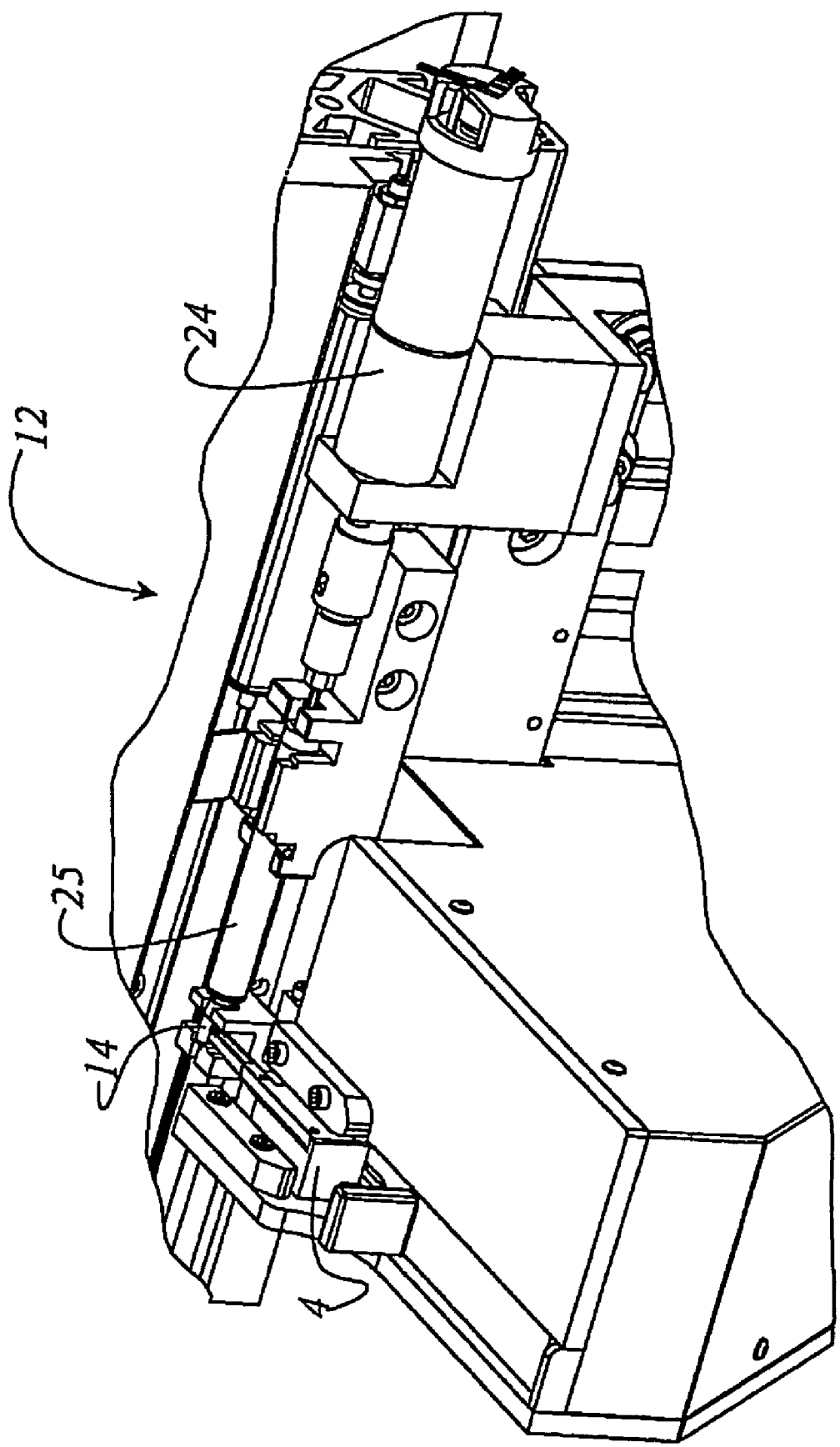
FIG. 5 is a perspective view of the automatic loading apparatus, the slider already being slid sufficiently far into the automatic loading device that the holder having the specimen is positioned in the clamping element.
Figure 8:
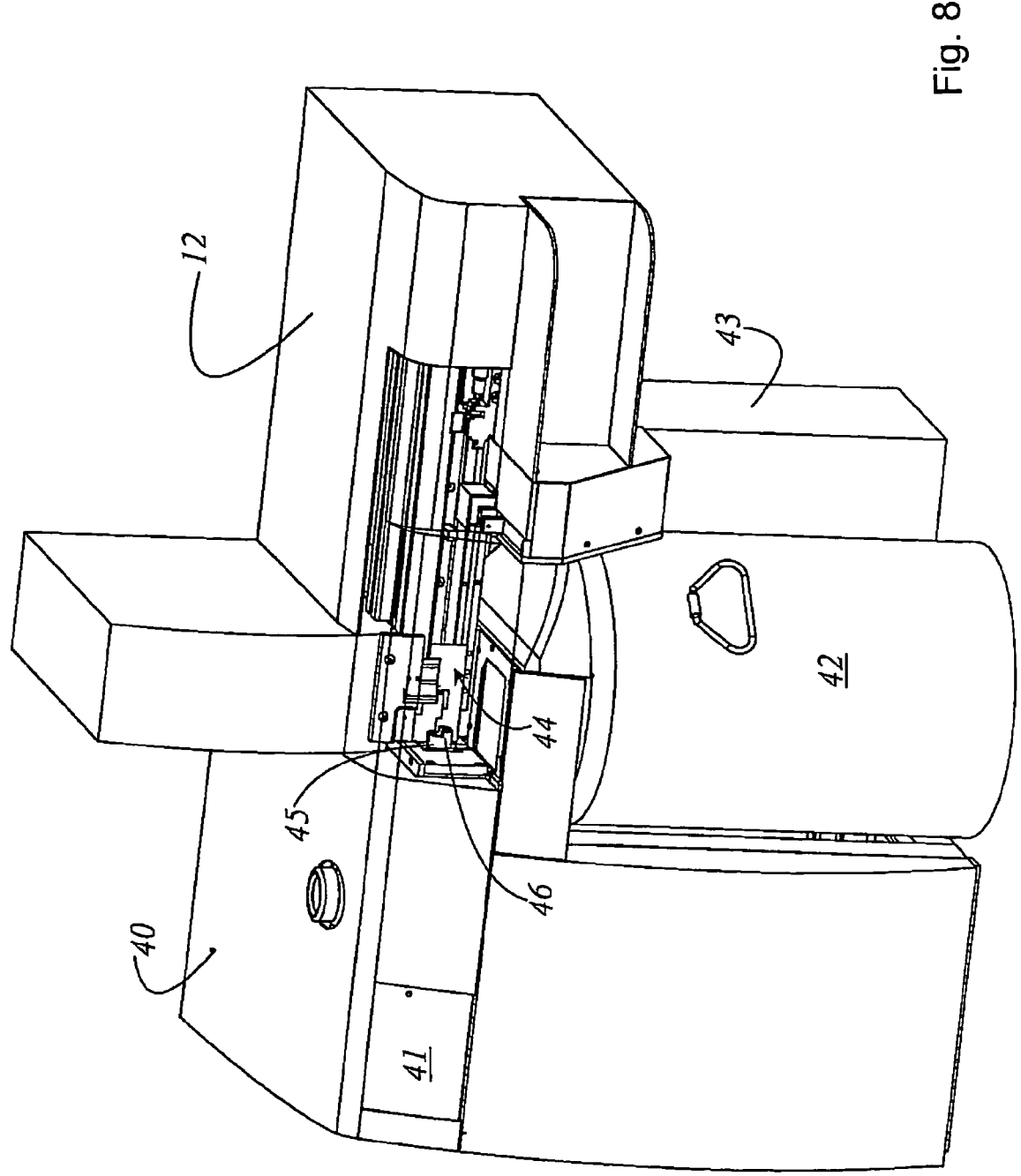

FIG. 1 is a perspective view of a slider 4 for introducing a specimen 1, secured in a holder 2, into an automatic loading apparatus 12 (see FIGS. 5 and 8). It is self-evident to one skilled in the art that the embodiment of the slider depicted here represents merely one exemplifying embodiment of several possible ones. The embodiment disclosed here is not to be construed as a limitation of the invention.

Slider 4 is embodied at one end with a grip element 5 with which a user can transport slider 4. A fork 3 is embodied at the end of slider 4 located opposite grip element 5. Fork 3 possesses a first limb 3a and a second limb 3b. A respective recess 7 is shaped into first limb 3a and into second limb 3b in the region of the open end 6 of fork 3. Recess 7 is configured in such a way that the holder is retained in a clamping fit by first limb 3a and second limb 3b. First limb 3a and second limb 3b are embodied elastically, so that a clamping force is exerted on holder 2 placed in recess 7. This clamping force allows the holder to be firmly retained in and securely fitted into in the fork during transport by a user.

Figure 2:
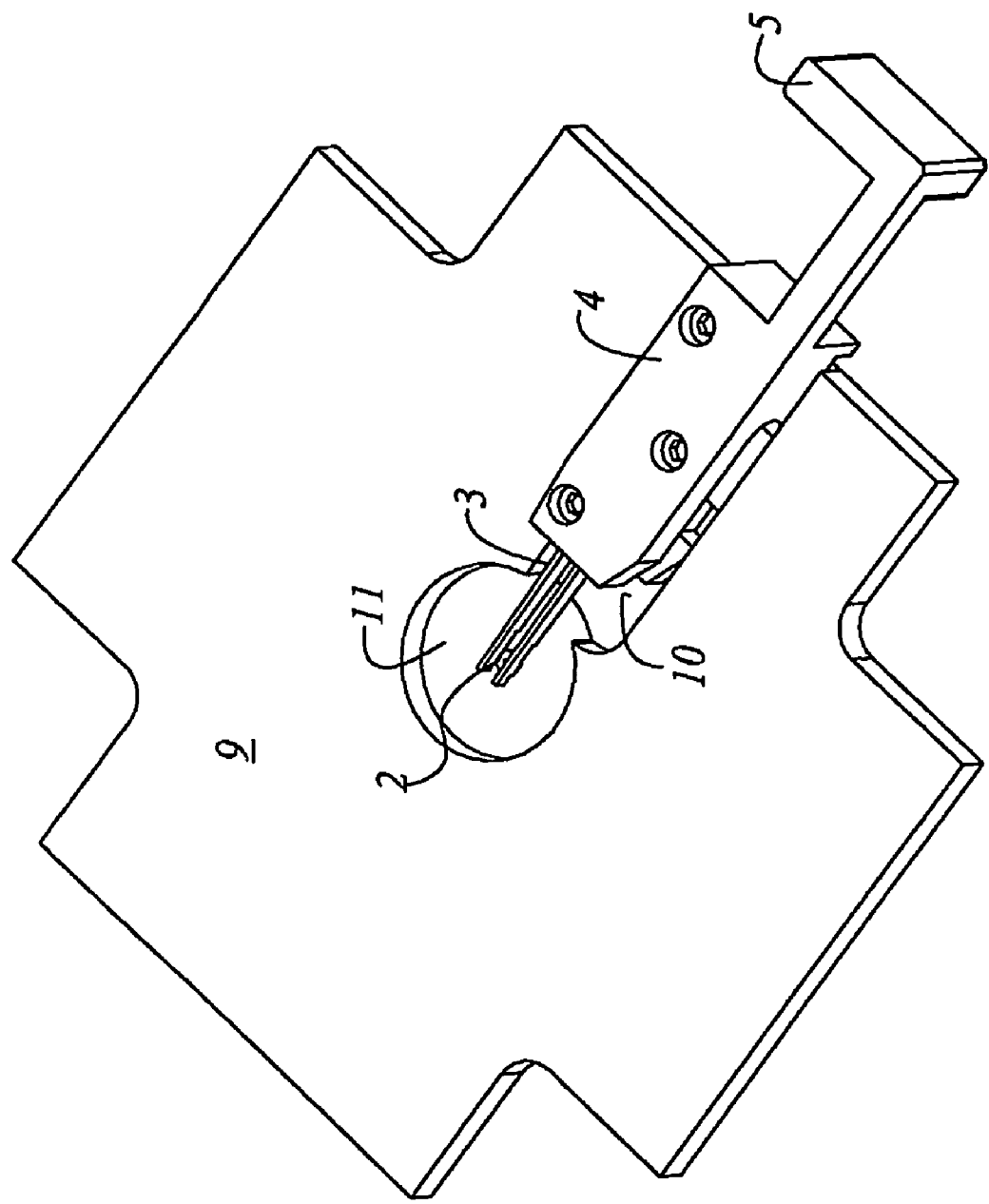
FIG. 2 is a perspective view of a microscope stage having a slider positioned thereon, so that the specimen located in the holder can be examined optically.

FIG. 2 is a perspective view of a microscope stage 9 of an optical microscope (not depicted). The microscope can be, for example, a confocal microscope. Microscope stage 9 is embodied with a cutout 10 into which slider 4, with a holder 2 having a specimen 1 and mounted in fork 3, is positioned for optical examination with the microscope. Cutout 10 in microscope stage 9 and slider 4 are configured in such a way that when a slider 4 is inserted into cutout 10, holder 2 and specimen 1 come to rest on a coverslip 11 provided on microscope stage 9. Oil immersion can also be used for optical examination of specimen 1 inserted in holder 2.

Figure 3:
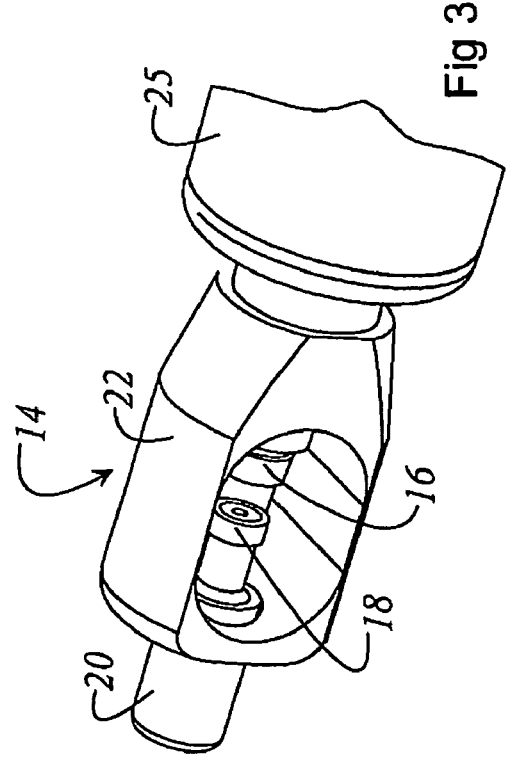
FIG. 3 is an enlarged depiction of a clamping element in which the holder having the specimen is clamped for high-pressure freezing.

FIG. 3 is a perspective view of a clamping element 14 in which holder 2, with specimen 1 located therein, is clamped or immovably retained. Clamping element 14 possesses a pusher part 16 that is arranged opposite a counterelement 18. Counterelement 18 is connected to a connector tube 20 for high pressure. Through the connector tube, high pressure is directed onto specimen 1 that is clamped between counterelement 18 and pusher part 16. Pusher part 16 can be displaced via a threaded screw (not depicted) so that it moves toward counterelement 18 and thus clamps holder 2 having specimen 1 in the clamping element. A motor shaft 25 engages on pusher part 16 and thus moves pusher part 16 toward or away from counterelement 18.

Figure 4:
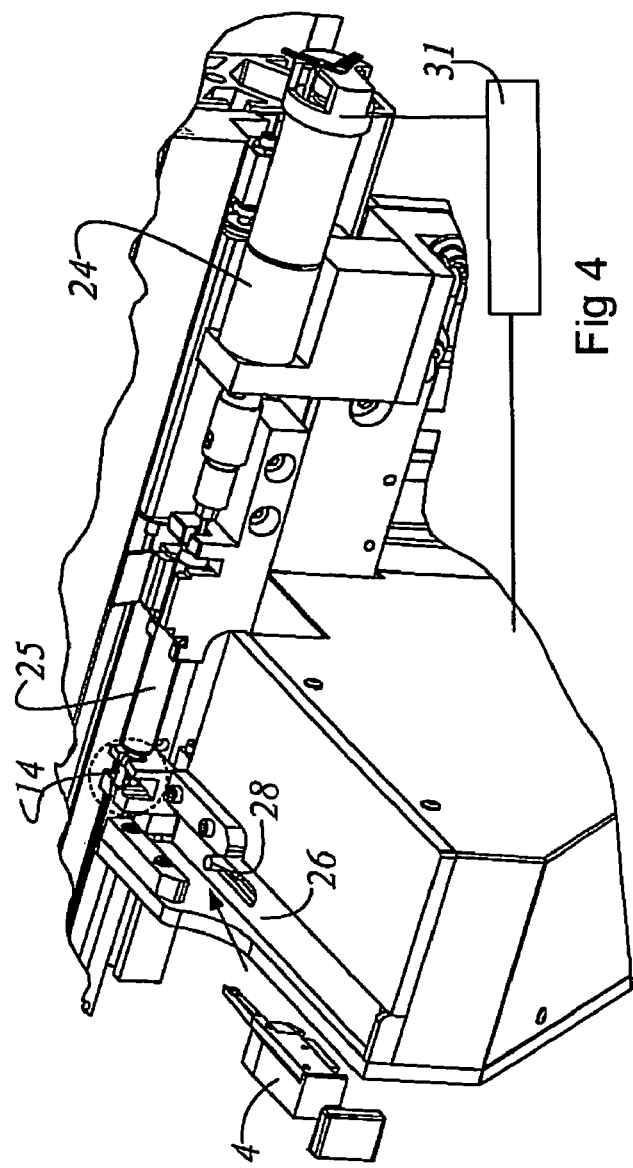
FIG. 4 is a perspective view of a portion of the automatic loading apparatus, the positioning aid for the slider likewise being depicted.

FIG. 4 is a perspective partial view of automatic loading apparatus 12, housing parts of automatic loading apparatus 12 having been omitted so as thereby to provide insight into the manner of operation of the automatic loading apparatus. Automatic loading apparatus 12 is substantially linear in construction. Associated with automatic loading apparatus 12 is a guidance element 26 with which holder 2 is positionable in clamping element 14. Clamping element 14 is positioned in automatic loading apparatus 12. Slider 4, which holds holder 2 having specimen 1 in fork 3, is inserted into guidance element 26. As a result of the linear displacement of slider 4 toward clamping element 14, holder 2 is positioned in the clamping element between counterelement 18 and pusher part 16. The linear displacement of the holder toward clamping element 14 also starts the automatic loading operation. For this, a corresponding switch (not depicted) is actuated. Automatic loading apparatus 12 encompasses a motor 24. From motor 24, motor shaft 25 extends toward clamping element 14. As already explained above, pusher part 16 can be moved with motor 24 toward counterelement 18 so as thereby to clamp the holder between pusher part 16 and counterelement 18. Automatic loading apparatus 12 likewise encompasses a sensor 28 that ascertains the presence of slider 4 in the automatic loading apparatus. A control system 31 is also connected to the motor and establishes, from the power consumption of motor 24, a torque-limited threading motion between counterelement 18, holder 2, and pusher part 16. This ensures that holder 2 is not crushed to an unnecessary extent by counterelement 18 and pusher part 16. Unnecessarily severe crushing could result in a change in the morphology of specimen 1 to be examined.

FIG. 5 is an enlarged perspective partial view of automatic loading apparatus 12, in which specimen 1 located in holder 2 has already been introduced into clamping element 14. Slider 4, which carries holder 2 having specimen 1 and is placed on guidance element 26, has been advanced toward clamping element 14. Motor shaft 25 is in contact with pusher part 16 of the clamping element. Pusher part 16 is then moved in threading fashion, with motor 24, toward counterelement 18. Holder 2 is thereby clamped between pusher part 16 and counterelement 18. Once clamping is achieved, the slider is pulled back.

Figure 6:
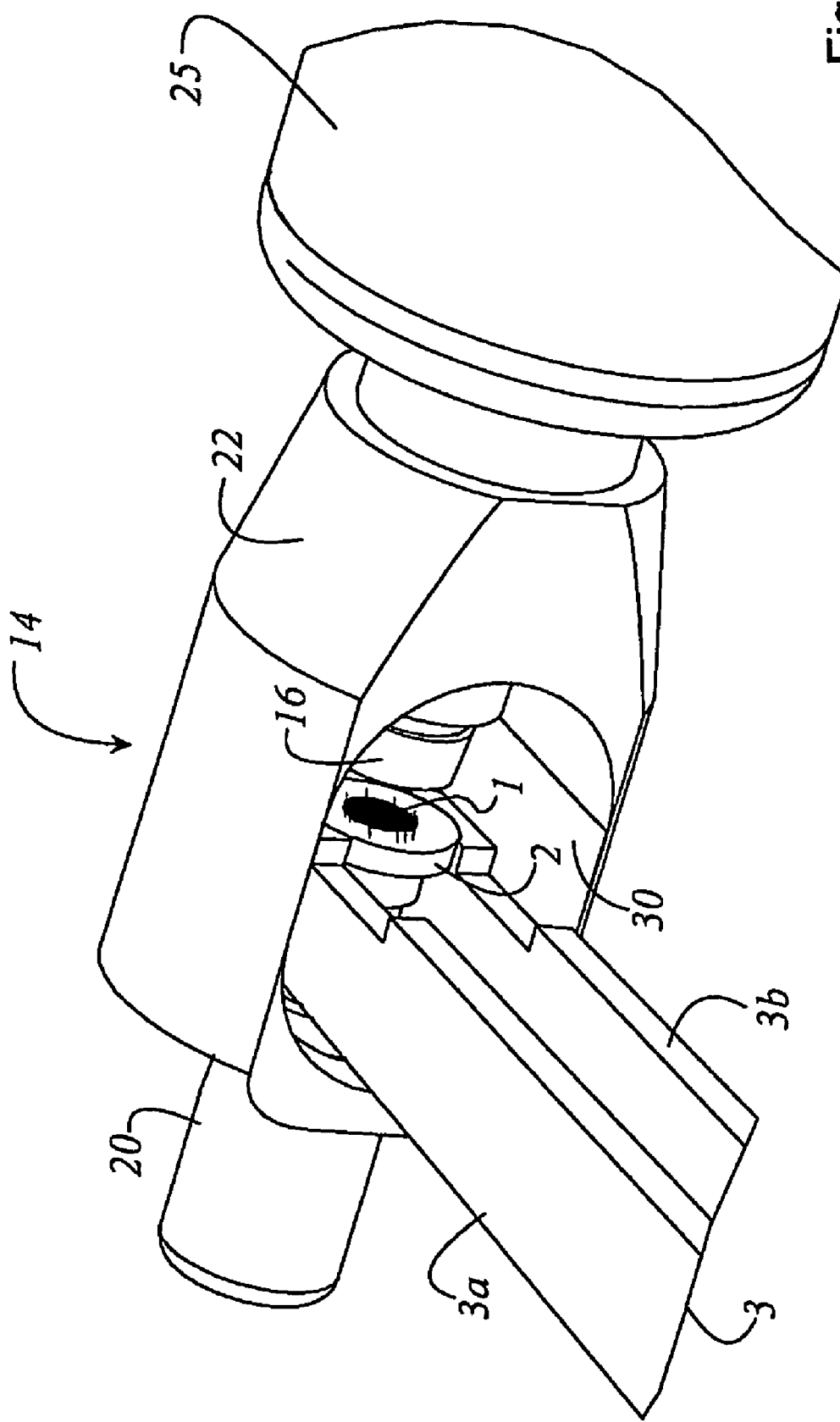
FIG. 6 is an enlarged perspective depiction of the clamping element, the holder having the specimen being positioned in the clamping element.

FIG. 6 is an enlarged depiction of clamping element 14 in which fork 3 with holder 2 is positioned between pusher element 16 and countermember 18. Before pusher part 16 is moved in threading fashion with respect to counterelement 18, sufficient clearance is present between pusher part 16 and counterelement 18 that fork 3, along with the holder retained in the fork and the specimen, can be introduced into this clearance between pusher part 16 and counterelement 18. Clamping element 14 comprises a shell 22 that possesses two oppositely located openings 30. Because of openings 30 embodied in shell 22 of clamping element 14, the fork can be positioned between pusher part 16 and counterelement 18 so that holder 2 is clamped when pusher part 16 is moved in threading fashion with respect to counterelement 18.

Figure 7:
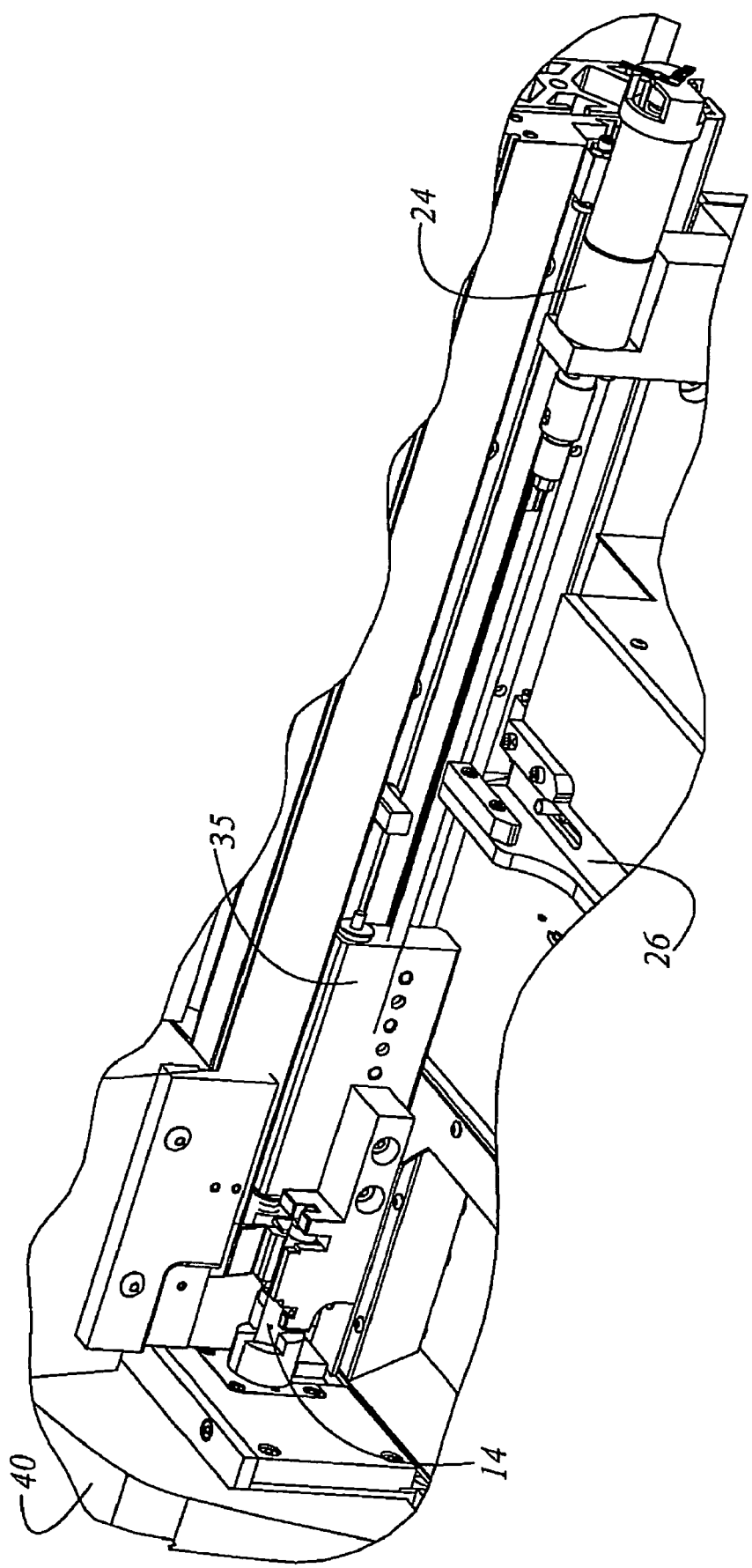
FIG. 7 is an enlarged perspective partial view of the automatic loading apparatus, the motor provided for closing the clamping element being uncoupled from the clamping element; and, FIG. 8 is a perspective overall view of a high-pressure freezing device to which the automatic loading apparatus for introducing the clamping elements into the high-pressure freezing device is connected.

FIG. 7 is an enlarged perspective partial view of automatic loading apparatus 12, in which clamping element 14 has been slid into high-pressure freezing device 40. Motor 24 is uncoupled from clamping element 14. Clamping element 14 is slid into high-pressure freezing device 40 by means of a pneumatic cylinder 35. In high-pressure freezing device 40, the connection for high pressure is made to connector tube 20 of clamping element 14. Pressure on the specimen can be built up via connector tube 20 of clamping element 14. Pneumatic cylinder 35 exerts sufficient pressure to ensure the connection for high pressure, and so that no pressure leakage occurs. A slider 4 is no longer inserted on guidance element 26. After high-pressure cryosubstitution is complete, automatic loading apparatus 12 is once again ready to receive a slider 4 with a holder 2, having a specimen, secured therein.

FIG. 8 is a perspective view of a high-pressure freezing device 40 having an automatic loading apparatus 12 mounted thereon. A display 41 is embodied on the housing of high-pressure freezing device 40. Display 41 can be embodied as a touch screen with which the user can enter parameters for the high-pressure freezing that is to be carried out. A reservoir 42, containing liquid nitrogen for cooling clamping element 14, is also connected to high-pressure freezing device 40. An electronic system or control system 43 that controls and regulates execution of the high-pressure freezing operation is also accommodated in the housing of high-pressure freezing device 40. Control system 43 additionally serves to synchronize the high-pressure freezing procedure. As already mentioned, the specimen is pressurized via connector tube 20 of clamping element 14. Immediately thereafter, liquid nitrogen is sprayed onto the clamping element in order to achieve appropriate cooling. The intensity of the pressure can be adjusted within a range from 1 to 2100 bar. High-pressure freezing device 40 is embodied with a chamber 44 in which high-pressure freezing takes place. An outlet 46 for high pressure is embodied on one sidewall 45 of chamber 44. The connection for high pressure to connector tube 20 of the clamping element is made at this outlet 46. This is accomplished, as already mentioned, through the pneumatic cylinder.

What is claimed is:

1. A high-pressure freezing device comprising: a chamber suitable for high-pressure freezing; a specimen holder retained in a clamping element; a reservoir of liquid nitrogen; an automatic loading apparatus comprising a slider and at least one guidance element; and, a sensor arranged to record the presence of the slider in the automatic loading apparatus, wherein the slider carries the specimen holder, the at least one guidance element arranged to position the specimen holder in the clamping element by means of the slider and the automatic loading apparatus is designed to transfer the clamping element into the chamber of the high-pressure freezing device, and wherein the clamping element comprises a pusher part, a shell and a counterelement and the shell comprises two oppositely located openings and partially encloses the pusher part and the counterelement.

2. The high-pressure freezing device as defined in claim 1, wherein a motor is provided which is connected via a shaft to a pusher part of the clamping element.

3. The high-pressure freezing device as defined in claim 2, wherein a control system is provided which establishes, from a power consumption of the motor, a torque-limited threading motion between a counterelement, the specimen holder, and the pusher part.

4. The high-pressure freezing device as defined in claim 1, wherein a pneumatic cylinder is provided in the automatic loading apparatus, which cylinder introduces the clamping element, with the specimen holder, into the high-pressure freezing device and uncouples a shaft of a motor from the clamping element.

5. The high-pressure freezing device as defined in claim 4, wherein the clamping element comprises a connector tube for high pressure; and the pneumatic cylinder creates, in the high-pressure freezing device, a connection for high pressure to the connector tube of the clamping element.

6. An automatic apparatus for loading specimens into a high-pressure freezing device comprising: a slider having a specimen holder retained thereon; at least one guidance element arranged to position the specimen holder in a clamping element; and, a sensor arranged to record the presence of the slider in the automatic apparatus for loading specimens, wherein the slider comprises a fork, the fork comprises two oppositely located limbs, each of the two oppositely located limbs comprises a recess mutually arranged to retain the specimen holder therein and wherein the clamping element comprises a pusher part, a shell and a counterelement and the shell comprises two oppositely located openings and partially encloses the pusher part and the counterelement.

7. The automatic loading apparatus as defined in claim 6, wherein a motor is provided which is connected via a shaft to a pusher part of the clamping element.

8. The automatic loading apparatus as defined in claim 7, wherein a control system is provided which establishes, from a power consumption of the motor, a torque-limited threading motion between a counterelement, the specimen holder, and the pusher part.

9. The automatic loading apparatus as defined in claim 8, wherein a pneumatic cylinder is provided which introduces the clamping element, with the specimen holder, into the high-pressure freezing device and uncouples the shaft of the motor from the clamping element.

10. The automatic loading apparatus as defined in claim 9, wherein the clamping element comprises a connector tube for high pressure; and the pneumatic cylinder creates, in the high-pressure freezing device, a connection for high pressure to the connector tube of the clamping element.

11. The automatic loading apparatus as defined in claim 6, wherein for examination with an optical microscope, a cutout is shaped into a stage support of the optical microscope; the slider is configured in such a way that the specimen holder having a sample therein, inserted into a fork, comes to rest on a coverslip located on the stage support.

* * * * *